(12) United States Patent
Krug et al.

(10) Patent No.: US 9,185,908 B2
(45) Date of Patent: Nov. 17, 2015

(54) DISINFECTANT FOR DISPLAY SCREEN SURFACES OF ELECTRONIC DEVICES COMPRISING A TERNARY MIXTURE OF ALCOHOLS

(75) Inventors: Barbara Krug, Hamburg (DE); Stephanie Fehling, Horst (DE); Richard Bloβ, Rellingen (DE)

(73) Assignee: Bode Chemie GmbH, Hamburg (DE)

( * ) Notice: Subject to any disclaimer, the term of this patent is extended or adjusted under 35 U.S.C. 154(b) by 0 days.

(21) Appl. No.: 14/110,259

(22) PCT Filed: Apr. 5, 2012

(86) PCT No.: PCT/EP2012/001519
§ 371 (c)(1),
(2), (4) Date: Oct. 7, 2013

(87) PCT Pub. No.: WO2012/136372
PCT Pub. Date: Oct. 11, 2012

(65) Prior Publication Data
US 2014/0030305 A1    Jan. 30, 2014

(30) Foreign Application Priority Data

Apr. 8, 2011 (DE) .......................... 10 2011 016 452

(51) Int. Cl.
| | | |
|---|---|---|
| C11D 1/88 | (2006.01) | |
| C11D 1/90 | (2006.01) | |
| C11D 3/43 | (2006.01) | |
| C11D 3/48 | (2006.01) | |
| A01N 31/02 | (2006.01) | |
| A01N 37/44 | (2006.01) | |
| A61L 2/18 | (2006.01) | |

(52) U.S. Cl.
CPC ................ *A01N 31/02* (2013.01); *A01N 37/44* (2013.01); *A61L 2/18* (2013.01); *A61L 2202/20* (2013.01)

(58) Field of Classification Search
CPC .......... C11D 1/88; C11D 1/90; C11D 3/2003; C11D 3/2006; C11D 3/201; C11D 3/43; C11D 3/48; C11D 7/261; C11D 7/5077; C11D 11/0023; C11D 11/0035
See application file for complete search history.

(56) References Cited

U.S. PATENT DOCUMENTS 5,454,983 A * 10/1995 Michael et al. ............... 510/102

FOREIGN PATENT DOCUMENTS

| DE | 198 01 821 A1 | 7/1999 |
|---|---|---|
| DE | 10 2007 010 939 | 9/2008 |
| EP | 1 020 115 | 7/2000 |
| EP | 1 362 512 | 11/2003 |
| EP | 1 468 699 A1 | 10/2004 |
| EP | 1468699 * | 10/2004 |
| EP | 1 967 066 A2 | 9/2008 |
| WO | WO 98/53681 | 12/1998 |
| WO | 2004003126 * | 1/2004 |
| WO | WO 2004/003126 | 1/2004 |

OTHER PUBLICATIONS

Bacillol 30 foam product literature, Jan. 30, 2012.*
PCT International Preliminary Report on Patentability, dated Oct. 8, 2013, issued in international application PCT/EP2012001519, 12 pages.
"Bacillol 30 Foam:Alcohol-based rapid disinfection," Feb. 1, 2011, p. 1-3, XP55029913,URL http://www.bode-chemie.com/products/surfaces/project-information/bacillol_30_foam_int.pdf.
German Search Report, dated Feb. 1, 2012, issued in priority application DE 10 2011 016 452.9, 4 pages.
"Bacillol 25:Alcohol-based rapid disinfection," Mar. 2009, product information pamphlet from Bode Chemie GmbH.
Management-Krankenhaus.de, Bacillol 30 Foam—Rapid Disinfection of Sensitive Surfaces, Jan. 30, 2012, URL: http://www.management-krankenhaus.de/produkte/hygiene/bacillol-30-foam-schnell-desinfektion-sensibler-oberflaenchen.
Standard Test Methods of DGHM, HygMed 2007, 32 (4), S 128-129. Standardmethoden der DGHM zur prufung chemischer desinfektionsverfahren, Gebel et al., Sep. 2001, mhp—Verlag GmbH (58 pages)(English translation of relevant portions only).
Bacillol AF, Alkoholische Schneildesinfection, Bode-Science-Competence, May 2007 (6 pages), (updated Dec. 2009; two English translations show May 2007 and Dec. 2009 content).
Bacillol 25, Alkoholische Schneildesinfection, Bode-Science-Competence, Nov. 2005 (4 pages).
Safety Data Sheet, Bacillol 25, according to 1907/206/EC, Article 31, Sep. 12, 2008 (5 pages).

* cited by examiner

*Primary Examiner* — Charles Boyer
(74) *Attorney, Agent, or Firm* — Nash and Titus, LLC

(57) ABSTRACT

The invention relates to a method for disinfecting display screen surfaces of electronic devices. Mobile communication devices, especially those which a reused in the medical sector, have plastic surfaces, often in the form of display screen surfaces. These surfaces cannot be disinfected with conventional alcoholic disinfectants. The disinfectant used in this invention contains a mixture of ethanol, 1-propanol and 2-propanol, an antimicrobial, amphoteric surfactant and water. This disinfectant enables effective eradication of microorganisms such as fungi, bacteria and yeasts, and has the further advantage of being compatible with the materials of the surfaces.

18 Claims, 2 Drawing Sheets

DISINFECTANT FOR DISPLAY SCREEN SURFACES OF ELECTRONIC DEVICES COMPRISING A TERNARY MIXTURE OF ALCOHOLS

This application claims priority from International Application PCT/EP2012/001519, filed Apr. 5, 2012, and German patent application DE 10 2011 016 452.9, filed Apr. 8, 2011, and the contents of these documents are incorporated by reference herein in their entirety.

BACKGROUND OF THE INVENTION

The invention has as subject matter the use of a disinfectant consisting of a mixture of ethanol, 1-propanol and 2-propanol, an antimicrobial, amphoteric surfactant and water for the disinfection of display screen surfaces of electronic devices.

Hygiene is an aspect in modem patient care that is becoming increasingly more important. The focus of many hygienic measures is the disinfection of hands as well as of surfaces without microorganisms. In particular those surfaces must be disinfected that come in contact with the hands, i.e., hand contact surfaces. Surfaces close to patients are usually treated with alcoholic disinfectants. These surfaces and planar objects such as, for example, tables, trays, chairs, doors, door handles, shelves, etc. are usually manufactured from alcohol-resistant materials. They concern primarily "stationary" objects that are subjected to a routine cleaning and disinfection.

The disinfection of objects that are not connected to a location is more difficult. For example, electronic devices are increasingly used for patient care. These modem media make it possible that diagnoses, laboratory results, digital presentations such as x-ray images and the like can be stored and transmitted. This means more certainty in the treatment since fewer transmission errors occur and the relevant information can be rapidly retrieved.

There is the disadvantage that these devices can pass from one patient room into the next one without being disinfected in the meantime. Therefore, the using of these mobile communication devices involves an elevated risk for the transmission of pathogenic germs. The published hygiene regulations state that the hands must be disinfected before and after each contact with a patient. However, if germs pass during the treatment onto mobile communication devices, the latter are not usually subjected to a routine disinfection since they are usually inserted for practical reasons into the coat pocket and are therefore not visible at first. There is therefore the danger that electronic devices, in particular mobile communication devices, are overlooked during the disinfection.

Corresponding devices are used not only in medical and nursing institutions but more and more also in the OP area and in intensive care units. An effective disinfection of all surfaces is necessary in particular in these sensitive hygienic areas in order to avoid a transmission of germs and resulting infections.

Mobile communication devices frequently have surfaces of plastic or glass, optionally also composite materials with a thin, multi-layer construction. In the disinfection of surfaces without microorganisms alcoholic disinfectants are customarily used. Thus, a disinfectant for rapid disinfection is known from EP 1 020 115 A1 that contain 68-80 wt % of a mixture of monoalcohols. These disinfectants also display a good effectiveness against viruses, fungi and bacteria on account of the high alcohol content.

In particular plastic surfaces are partially dissolved by organic solvents such as alcohol or acetone. In addition, many plastics contain softeners that are soluble in organic solvents and are thus washed out during the disinfection. The material therefore loses elasticity by being multiply treated with a disinfectant. This effect can be recognized by opacity and the formation of fissures in transparent plastics.

Mobile communication devices are distinguished by multifunctional properties. The so-called "smart phones" are operated in a simple manner via a touch display. The input surface is technically comparable to a transparent sheet keyboard consisting of a polyester sheet that is placed over a display, e.g., an LED or a liquid crystal display.

The displays of mobile communication devices are frequently provided with a protective display sheet in order to protect them from scratches and other external influences. These protective sheets are very resistant to scratches and impacts and have a crystal-clear optics and pleasant haptics with unlimited ability to use the devices. These protective sheets are usually multilayer laminates that unite the properties of the individual components. They usually consist of acrylic acid polymers, polycarbonate or of other known materials.

Previously, no alcoholic disinfectants were obtainable on the market that were suitable for the disinfection of mobile communication devices, in particular for the disinfection of display screens and touchscreens.

Disinfectants are known for the disinfection of surfaces without microorganisms that have a good compatibility with materials for certain surfaces of traditional objects and devices. EP 1 468 699 A1 discloses the use of a disinfectant based on an aliphatic monoalcohols and on an amphoteric surfactant in aqueous solution for the eradication of mycobacteria. This disinfectant displays a good material compatibility with Plexiglas.

On the other hand, it is known for alcoholic disinfectants with low alcohol contents that they have no comprehensive microbiocidal and in particular no fungicidal effectiveness.

SUMMARY OF THE INVENTION

The invention therefore addresses the problem of making a disinfectant available that displays good material compatibility with plastic surfaces of electronic devices, in particular of mobile devices that are used primarily in the medical area and require a professional disinfection, in particular their display screen surfaces such as touchscreens, and at the same time have a good microbiological effectiveness, in particular also a fungicidal effectiveness. The disinfectant should be able to be used with very different materials universally and independently of the material components and material properties based on the good material compatibility since it is to be assumed that not only the transparent display surface but also the entire housing of the corresponding devices comes in contact with the disinfectant and that different components of an electronic device consist of different plastics.

The problem is solved in accordance with the invention by the usage of a disinfectant containing 25-32 wt % of a mixture of ethanol, 1-propanol and 2-propanol, whereby at least 5.0 wt % and at the most 15 wt % of each individual alcohol component are contained, and
0.1-2.0 wt % of an antimicrobial, amphoteric surfactant and water for the disinfection of display screen surfaces of electronic devices, in particular flat display screens, laptop display screens, touchscreens, mobile telephone displays, smart phones, tablet PCs and PDAs.

Other embodiments constitute subject matter of the dependent claims or are described in the following.

DESCRIPTION OF THE PREFERRED EMBODIMENTS

Figure 1:
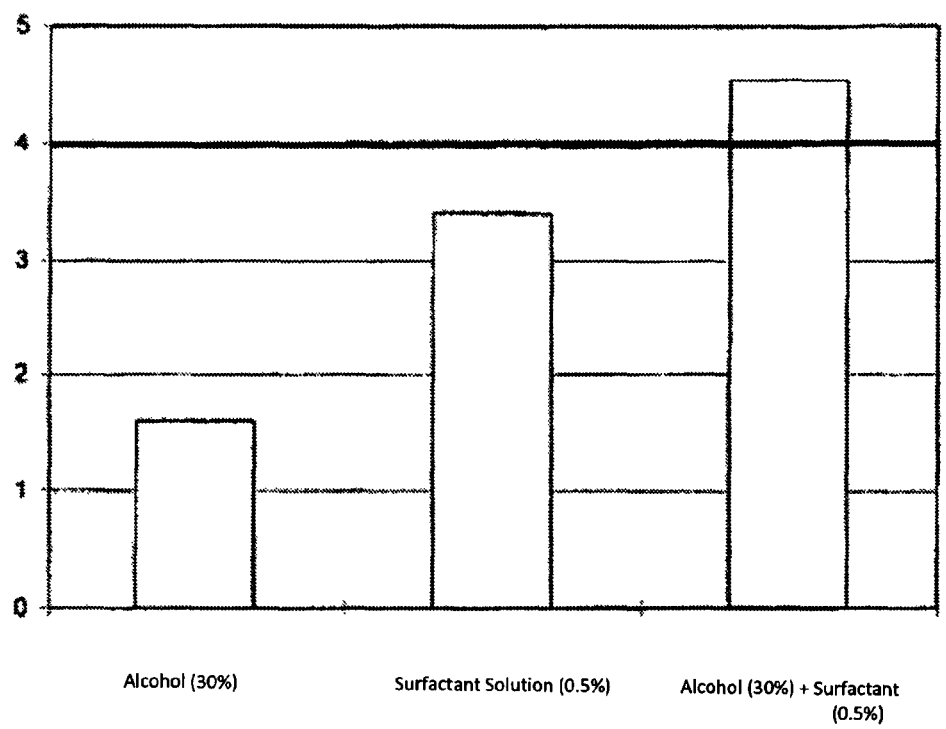
FIG. 1 shows the microbiological activities against *Candida albicans* (0.5 minutes).

The disinfectant used in accordance with the invention preferably consists of
- 25-32 wt % of a mixture of ethanol, 1-propanol and 2-propanol, whereby at least 5.0 wt % and at the most 15 wt % of each individual alcohol component are contained, and
- 0.1-2.0 wt % of an antimicrobial, amphoteric surfactant and water, whereby the components supplement each other to 100 wt %.

The disinfectant used in accordance with the invention preferably contains 28-32 wt % of the mixture of ethanol, 1-propanol and 2-propanol. Furthermore, the disinfectant preferably contains 0.1-1.0 wt % surfactant.

The disinfectant used in accordance with the invention furthermore preferably contains
- 13 to 15 wt % ethanol,
- 9 to 10.5 wt % 2-propanol,
- 5 to 6.5 wt % 1-propanol,
- 0.1 to 2.0 wt %, preferably 0.1 to 1.0 wt % of an antimicrobial, amphoteric surfactant and
water, preferably as residual water.

The antimicrobial, amphoteric surfactant used is preferably N-alkylaminopropyl glycine, whereby the alkyl group has 10 to 16 carbon atoms. Such a surfactant is obtainable as a 30% aqueous solution under the trade name Rewocid WK 30 of the Evonik company.

The display screen surfaces of electronic devices disinfected in accordance with the usage of the invention are in particular the display screen surfaces of touchscreens, mobile telephones, smart phones, flat display screens, laptop display screens, tablet PCs and PDAs, whereby in particular the displays and/or touchscreens or the protective sheets applied on these devices are disinfected. The disinfected surfaces consist preferably at least partially of temperature-resistant or transparent or highly reflective plastics or plastic coatings, preferably of polycarbonate or polysulfone. A known polycarbonate is, for example, Makronon® and a known polysulfone is, for example, Tecason®.

The usage of the disinfectant in accordance with the invention results in the eradication of yeasts in particular of *Candida albicans* and/or in the eradication of fungi, in particular of *Aspergillus brasiliensis* (earlier designation *Aspergillus niger*). When the disinfectant is used in accordance with the invention a log 4 reduction preferably takes place within 0.5 minutes opposite *Candida albicans* and/or a log 4 reduction within 1 minute opposite *Candida albicans* according to the "Standard methods of the DGHM for the testing of chemical disinfection methods" (state Sep. 1, 2001). Furthermore, the usage of the disinfectant in accordance with the invention preferably achieves at least a log 2 reduction within 5 minutes opposite *Aspergillus brasiliensis* and/or at least a log 3 reduction within 10 minutes opposite *Aspergillus brasiliensis* and/or a log 4 reduction within 15 minutes opposite *Aspergillus brasiliensis* according to the "Standard methods of the DGHM for the testing of chemical disinfection methods" (state Sep. 1, 2001).

The method "Standard methods of the DGHM for the testing of chemical disinfection methods" (state Sep. 1, 2001) is equivalent in execution and evaluation to the international EN 13727 ("Chemical disinfectants and antiseptics—Quantitative suspension experiment for the testing of the bactericidal effect of chemical disinfectants for instruments in the area of human medicine—Test methods and requirements (phase 2, stage 1); German version EN 13727:2003). The test germ *Aspergillus brasiliensis* ATCC 16404 corresponds to the germ *Aspergillus niger* ATCC 16404 (earlier designation) and is genetically identical to the latter.

The disinfectant used in accordance with the invention is preferably applied in the form of a foam, a spray disinfectant, a liquid or in the form of a cloth, sponge or other application aid impregnated with the disinfectant.

The liquid composition can be applied on a cloth and used in the form of a wiping disinfection. However, it can also be sprayed, in which case the composition is sprayed either as a liquid or preferably by a dispenser with foam applicator as foam. The foam can be applied directly onto the surface to be cleaned or by a cloth, a sponge or by another application aid. The composition comprises no other constituents and in particular no other components are required for stabilizing the foam.

The disinfectant used in accordance with the invention unexpectedly allows a comprehensive eradication of yeasts and fungi in spite of the low alcohol content and thus has a very good microbiological and especially fungicidal effect. The microbiological effect in particular against problem germs such as yeasts and fungi is clearly greater than that of the individual components and can be traced to a synergistic effect of the alcohol mixture in a mixture with the amphoteric surfactant. The good effect against fungi such as *Aspergillus brasiliensis* is just as surprising. Here too, it was not to be expected based on the effectiveness of the individual constituents that a good reduction of germs is achieved with so low an alcohol concentration. In spite of the low alcohol content the disinfectant used in accordance with the invention also displays a good effect against uncoated viruses that are difficult to inactivate such as, e.g., adenoviruses.

In addition, there is a good compatibility with materials when using the disinfectant in accordance with the invention so that the disinfectant can also be used on the sensitive display screen surfaces of electronic devices such as, e.g., flat display screens, touchscreens, PDAs, mobile telephones, keyboards and in particular plastic surfaces with polysulfone or on the protective sheets applied on them.

The disinfected display screens of the electronic devices disinfected in accordance with the use according to the invention are in particular the display screens of touchscreens (for example, on operating terminals), mobile telephones, smartphones, for example, iPhone®, Blackberry®, flat display screens, laptop display screens, tablet PCs, beepers and PDAs, whereby in particular the displays and/or touchscreens or the protective sheets of these devices applied on them are disinfected. The usage in accordance with the invention concerns all surfaces of such devices that make contact with the hands and/or other skin surfaces of doctors, nurses, caretakers and patents, in particular hand contact surfaces.

The devices are present preferably in the area of clinical and nursing facilities such as treatment rooms, stations, patient rooms, examination rooms, operating rooms, delivery rooms, ambulances, intensive care units in nursing facilities, hospitals and physicians' practices as well in in mobile nursing care. The disinfectant used in accordance with the invention is employed in particular in medical and nursing facilities, preferably in the OP area and in intensive care units, medical units and nursing units. In them a professional disinfection of all surfaces is necessary in order to avoid a transmission of germs and resulting infections.

The disinfection takes place on surfaces consisting at least partially of plastics. If plastic materials are mechanically expanded or stressed below the elastic limit, after a certain time stress fissures can appear in the material. The simultaneous stressing in the presence of a changed chemical environment can result in a significant shortening of this time period. This phenomenon is designated as environmental stress cracking, ESC.

The disinfectant used in accordance with the invention is distinguished in particular by its good material compatibility. When the disinfectant is used in accordance with the invention on polysulfone surfaces the material compatibility of the disinfectant is preferably measured as ESC potential $\Omega_{ESC}$ according to an alternating ESC test <1, preferably <0.8 for a test time of 25 minutes at 25° C. In addition, when the disinfectant is used in accordance with the invention on polysulfone surfaces the environmental stress cracking $\Delta\Omega_{ESC}$ is preferably below 5, preferably below 4, furthermore preferably below 3 according to the ESC test at a surface temperature of 20° C. to 45° C.

Another aspect that plays a part in the disinfection of surfaces are possible residues produced by the preparation. The disinfectant used in accordance with the invention is a leave-on product that does not have to be removed after the disinfection. Therefore, when used, no disturbing residues remain on the surface that would adversely affect the readiness for use of the electronic device. In addition, the product should not be irritating, since the skin surface comes in contact with the display screen surface and/or keyboards when the devices are used and possible residues of the disinfectant used in accordance with the invention thus can be transferred onto the skin. It was shown that the residues of the disinfectant used in accordance with the invention that remain on the surface do not have an irritating effect on the skin since the alcohols evaporate after use and only slight amounts of the amphoteric surfactant remain and preferably contain no other constituents.

Therefore, the disinfectant used in accordance with the invention is also distinguished that the composition preferably contains no other alcohols, no other active substances, no quaternary ammonium compounds (QAV) and no non-ionic, anionic or cationic surfactants. The use in accordance with the invention for the disinfection of display screen surfaces can of course be used not only in the medical and clinical areas but also in other areas. Thus, the disinfection in public facilities, in particular in vending machines with touchscreens, in the food industry, hotels in automatic ticket machines or automatic teller machines, public information terminals and many other areas is conceivable.

EXAMPLES

A disinfectant was produced from the constituents indicated in table 1.

TABLE 1

|  | Example 1 |
| --- | --- |
| Aqua purificata | 69.50% |
| Ethanol | 14.00% |
| 2-Propanol | 10.00% |
| 1-Propanol | 6.00% |
| N-alkylaminopropyl glycine (alkyl equal to C 10 to C 16) | 0.50% |

The composition has a pH of 8.

The disinfectant according to table 1 was tested for its effectiveness against yeasts and fungi in comparison to solutions of individual components according to table 2. For this, the following comparison solutions were prepared:

TABLE 2

|  | Aqueous solution alcohols | Aqueous solution surfactant |
| --- | --- | --- |
| Aqua purificata | 70.00% | 99.50% |
| Ethanol | 14.00% | — |
| Isopropanol | 10.00% | — |
| n-Propanol | 6.00% | — |
| N-alkylaminopropyl glycine (alkyl equal to C 10 to C 16) | — | 0.50% |

Figure 2:
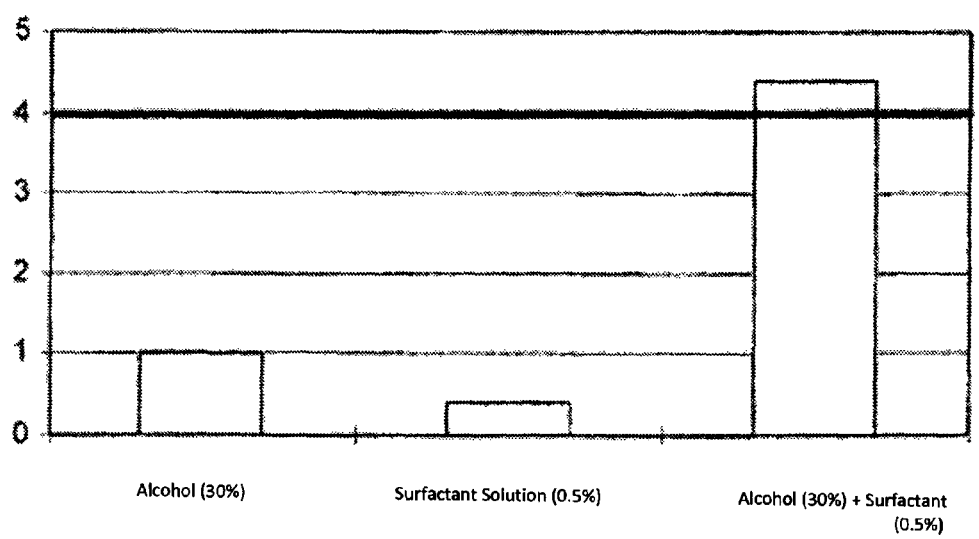
FIG. 2 shows the microbiological activities against *Aspergillus brasiliensis* (15 minutes).

In the figures:

FIG. 1 shows the microbiological activities against *Candida albicans* (0.5 minutes) and FIG. 2 shows the microbiological activities against *Aspergillus brasiliensis* (15 minutes).

FIG. 1 shows the microbiological activity of an aqueous alcohol mixture, of a pure aqueous surfactant solution according to table 2 and of the disinfectant mixture according to table 1 opposite *Candida albicans*. It can be recognized that only the disinfectant used in accordance with the invention achieves the required reduction of 4 log stages. The pure alcohol mixture does not achieve a sufficient reduction of the yeasts on account of the low alcohol content.

As can be recognized in FIG. 2, in the activity against fungi the effects of the individual constituents are not added to each other but rather a synergistic activity occurs by which the required reduction by 4 log stages is achieved.

Fungicide Test

The determination of the fungicidal effect in the quantitative suspension test according to the "Standard methods of the DGHM for the testing of chemical disinfection methods" (state Sep. 1, 2001) describes a test method and the minimum requirements for the fungicidal effect of chemical disinfectants and antiseptic products for determining whether an antiseptic has a fungicidal effect in the framework of the work area and field described in the area of application.

The products can only be tested in a concentration of 80% or less since a certain dilution is always brought about by the addition of the test germs and of the stressing substance.

The test germs for a disinfection of instruments and for surface disinfection are *Candida albicans* (ATCC 10231) and *Aspergillus brasiliensis* (ATCC 16404). *Aspergillus brasiliensis* is still designated as *Aspergillus niger* in the method "Standard methods of the DGHM for the testing of chemical disinfection methods" (state Sep. 1, 2001).

The test temperature is 20° C. and additionally 30° C. for an agent for surface disinfection and maximally 60° C. for an agent for instrument disinfection. The exposure time is 60 minutes and for an agent for surface disinfection the test is extended an additional 5 minutes. In addition, exposure times are tested in accordance with producer data.

Product test solutions are to be produced in at least three different concentrations in water of standardized hardness, whereby one concentration must be in the active range and one concentration in the non-active range. The product in the delivery state may be used as one of the product test solutions; in this case the highest tested concentration is 80%.

The number of cells in the test suspension is adjusted with the dilution agent to $1.5*10^8$ KBE per ml to $5.0*10^8$ KBE per ml.

The stressing substance must be selected in accordance with the application conditions determined for the product. It must be sterile and produced with a concentration ten times higher than is needed for the test. In the case of low stressing (clean condition) bovine serum albumin solution is used in a low concentration (0.3 g/l). In the case of high stressing (dirty condition) a mixture of bovine serum albumin solution in a high concentration (3 g/l) with washed sheep erythrocytes (3 ml/l) is used.

For the control, instead of a test suspension a validation suspension is used in which the test suspension is diluted in such a manner with the dilution agent that $3.0*10^2$ KBE per ml to $1.6*10^3$ KBE per ml result.

1 ml stressing substance and 1 ml test suspension were pipetted into a test tube. The stopwatch was started immediately, a thorough mixing carried out and the test tube placed for 2 min+/−ten s into a water bath adjusted to 20° C. After the passage of this time 8 ml of one of the product test solutions was added. The stopwatch was started again at the beginning of the addition, a thorough mixing carried out and the test tube placed for the selected exposure time t into a water bath adjusted to 20° C.

Immediately before the end of t the solution was thoroughly mixed again. After the passage of t a 1 ml sample of the test mixture was transferred into a test tube with 8.0 ml neutralization medium and 1 ml water. It was thoroughly mixed and placed into a water bath adjusted to 20° C. After a neutralization time of 5 min+/−10 s it was thoroughly mixed and a sample of 1 ml of the neutralized test mixture (containing neutralization medium, product test solution, stressing substance and test suspension) was immediately removed as repeat determination and seeded in the surface method.

In addition, 0.5 ml of this mixture was transferred into a test tube containing 4.5 ml of the neutralization medium in order to obtain the neutralized test mixture in a dilution of $10^{-1}$. Samples of 1 ml were taken as repeat determination from each dilution test tube and seeded in the surface method.

When using the surface method, each 1 ml sample, that was divided into amounts of about the same size, was spread out onto a suitable number (at least two) of plates dried on the surface.

The plates were incubated 20 h to 24 h and counted in order to determine the number of colony-forming units (KBE).

The result of the quantitative suspension test under high organic stressing in *Aspergillus brasiliensis* is shown in table 3.

TABLE 3

| Test times | Recipe according to example 1 Reduction factor | Recipe according to reference example 1 Reduction factor |
| --- | --- | --- |
| 5 min | 2.56 | 0.63 |
| 10 min | 3.58 | 0.80 |
| 15 min | 4.4 | 0.89 |

Virus Activity

For the testing of the inactivation of viruses eight volume fractions of the disinfectant were mixed (in accordance with the guidelines of the DVV and the RKI) with one volume fraction virus suspension and one volume fraction aqua bidest. In the tests with FKS stressing, instead of aqua bidest. one volume fraction of FKS stressing substance was added. Furthermore, nine volume fractions were mixed with 0.1 volume fraction virus suspension and 0.9 volume fractions aqua bidest. In the tests with stressing, instead of aqua bidest. FKS stressing substance was added.

All test preparations were carried out in closed plastic test tubes in a water bath at 20° C.+/−0.5% C. After the passage of the exposure times, partial amounts were removed from the plastic test tubes and the residual infectiosity determined. The determination of the infectiosity took place with the aid of an endpoint titration in the microtiter method. For this, the samples were first diluted in an ice cold medium by a factor of 10 after they were taken and each 100 µl of the dilution were transferred into eight cavities of a sterile 96-well microtiter plate with previously placed CV-1 cells (10-15×103 cells each) and incubated at 37° C. in a CO2 incubator (5% CO2 content). After 21 days the evaluation of the preparations took place via examination with an inverse microscope.

The examination of the virus-inactivating effect of the disinfectant to be tested took place by calculating the titer drop in comparison to the control titrations without disinfectant carried out in parallel. The difference was indicated as the reduction factor with a confidence interval of 95%.

In the guideline the concepts "limited antiviral" (active against encased viruses) and "antiviral" (active against non-encased viruses" are used in the sense of the definition of the position of the virucide team of the RKI. The activity against non-encased viruses includes an activity against encased viruses. The test viruses for the effective range "limited antiviral" are vacciniavirus, strain Elstree3 and bovine viral diarrhea virus (BVDV), strain NADL. The test viruses for the effective range "antiviral" are vacciniavirus, strain Elstree3, polio virus inoculation strain type 1, strain LSc-2ab, adenovirus type 5, strain adenoid 75 and polyomavirus4 (SV 40), strain 777.

The viruses are to be multiplied in cell cultures or in other suitable systems. The methods used for producing the virus suspension can differ as a function of the test virus. The virus content of the suspensions should be not less than 108 TCID50/ml.

Since the disinfectant to be tested should be used non-diluted or in ready-to-use form commercially, the test takes place at a concentration of 90 or 80% of the product in the test solution as a consequence of the necessary addition of virus suspension and FKS stressing (fetal calf serum).

The disinfectant according to example 1 displayed a good virus activity within a maximum of 5 minutes with a reduction of at least 4 log stages for the viruses vaccinia virus, bovine viral diarrhea virus, polyoma virus and rota virus. Thus, a reduction of the virus titer greater than log 4 stages was achieved within 30 seconds for vaccinia virus and bovine viral diarrhea virus under organic stressing (10% FKS).

Material Compatibility Testing

In addition, the material compatibility of a recipe produced in accordance with example 1 was tested.

For the testing and evaluation of the environmental stress cracking, ESC in the bending strip method the composition according to example 1 was tested on the test materials Plexiglas® XT (PMMA, polymethylmethacrylate, Evonik), Makrolon® 281 (PC, polycarbonate, Bayer) and Tecason® S (PSU, polysulfone, Ensinger).

The tests were carried out in accordance with DIN EN ISO 22088 part 1 and 3 (former DIN 53449 part 3 "evaluation of the environmental stress cracking—bending strip method") in a climatic test cabinet with fleece moistening (DIN EN ISO 22088-1 plastics—determination of the resistance to environmentally conditioned environmental stress cracking (ESC)—part 1: General instructions (ISO 22088-1: 2006) and part 3: bending strip method (ISO 22088-3:2006)). In order to prevent a too rapid evaporation of the liquid test product, an inert fleece (Tecnojet A-650/1, Ahlstrom Milan) was used as surface support that at the same time ensured a complete moistening of the test piece surface. The ESC potential $\Omega_{ESC}$ can be used as an auxiliary means for evaluating obtained test data.

For the testing in accordance with DIN EN ISO 22088-1 plastic strips were arranged under constant bending tractive tension and exposed for a previously determined time to a medium causing stress fissures. An increasingly higher elongation was generated with a series of baffles with decreasing radii in the outer surface. After a set stressing by the medium causing stress fissures the test pieces were removed, subjected to a visual test and tested for the indicative property such as, e.g., tensile strength.

The production of the test pieces took place in accordance with ISO 2818. The dimensions of the test bodies were 120 mm×35 mm×3.0 mm (length l×width b×thickness d). The test pieces were conditioned prior to the testing at least 24 h at (23±2°) C. and 50±5% relative moisture. The testing temperature was 25° C. The testing took place with an alternating test sequence of 5 times 5 min contact with the disinfectant and 5 min rest pause without contact with the disinfectant. The test time period was 5, 10, 15 20 and 25 minutes. The bending baffle had a radius of 456 mm.

The bending tractive tension is the nominal value of the elongation in the surface, loaded with traction, of a flat test piece with thickness h, which is bent via a circular segment with the radius r. The elongation value is a value from a series of elongation values imposed on successive test pieces during the stressing. The ESC potential $\Omega_{ESC}$ is the ratio of the value of the elongation at break determined in the test medium to the elongation determined at the same stressing time in the reference medium (usually air). At a value >1 there is a tendency to form stress fissures at given test conditions.

Test stresses of 9.13 MPa were realized in the stress fissure tests carried out with the plastic material polysulfone.

In the comparison of the individual tests to the alternating test sequences it can be recognized in the 450 mm ring baffle that the alternating test sequences display more intensive influences in comparison to the individual tests. The alternating test sequence was used in a comparison test in a different chemical environment comparing the recipe according to example 1 and the surface disinfectant according to reference example 1. The result of this examination yielded for the recipe according to example 1 the lowest tendency to form stress fissures that were still clearly below the boundary limit of 1 in the expanded tests up to 25 minutes.

The result of the test at 25° C. with the plastic material polysulfone in an alternating test (5 min exposure time, 5 min recovery phase, 5 min exposure time, 5 min recovery phase, etc.) is shown in table 4.

TABLE 4

| Exposure time | Recipe according to example 1 ESC potential $\Omega_{ESC}$ | Recipe according to reference example 1 ESC potential $\Omega_{ESC}$ |
| --- | --- | --- |
| 5 min | 0.28 | 0 |
| 10 min | 0.31 | 0.31 |
| 15 min | 0.31 | 0.56 |
| 20 min | 0.47 | 0.81 |
| 25 min | 0.56 | 1.13 |

During the exposure time of 5 minutes the test piece was kept moist with the product. In the rest phase of 5 minutes the test piece dried. At an ESC potential $\Omega_{ESC}<1$ there is a tendency to form stress fissures under these test conditions. It becomes clear here that test pieces treated with the recipe in accordance with reference example 1 have the tendency to become damaged in that in this sample the ESC potential $\Omega_{ESC}$ exceeds the value 1 after a short time.

Table 5 shows the result of the test at 25° C. to 45° C. with the plastic material polysulfone taking into consideration the differences of the ESC potentials $\Delta\Omega_{ESC}$ at the particular temperatures—thus, the following dependency can be shown with $\Delta t$=constant (10 minutes, rise of $\Omega_{ESC}$ over the time from 5 to 15 minutes).

TABLE 5

| Temperature | Recipe according to example 1 $\Delta\Omega_{ESC}$ | Recipe according to reference example 1 $\Delta\Omega_{ESC}$ |
| --- | --- | --- |
| 25° C. | 0.4 | 0.4 |
| 35° C. | 0.8 | 1.6 |
| 45° C. | 2.3 | 5.7 |

The most pronounced temperature dependency is shown by the sample of the reference example 1 at which interaction reactions begin just below 35° C. that are not present or have not yet begun in the recipe according to example 1.

In addition, a series of examinations on the compatibility of different materials with the disinfectant were carried out. To this end test pieces from different materials were placed into the ready-to-use disinfectant for a period of 4 weeks and optically evaluated at regular intervals.

In order to determine the material compatibility, standardized test pieces of different materials were used (6×2 cm with a layer thickness according to the material of 1 to 3 mm):

Metals: Fine-grade steel, aluminum, copper, brass

Plastics: rubber (caoutchouc), polysulfone, latex PVC, polymethylmethacrylate (Plexiglas®), silicone, polystyrene, polytetrafluoroethylene (Teflon®, polycarbonate (Makrolon®), vinylidene fluoride-hexafluoropropylene-copolymerizate (Viton®, polyethylene, polypropylene, soft rubber (butadiene-caoutchouc).

For the preparation the test pieces were thoroughly cleaned with a neutral cleaner, washed with water and then air-dried. The test pieces were then individually placed into the ready-to-use disinfection solution in glasses with a screw-on cover at room temperature. The evaluation of the materials took place optically after: the 1st day, the 1st week, the 2nd week, the 3d week, the 4th week.

No corrosion occurred in any of the tested metals during the complete period of 4 weeks. No material damage occurred in any of the tested plastics. The disinfection solution used in accordance with the invention is not corrosive and does not damage materials under the test conditions carried out and can therefore can be considered as compatible with the above-cited materials.

In addition, in an application test close to practice different objects consisting of different materials were regularly treated with the disinfection solution for a longer time period. The objects were flat display screens/monitors/touchscreens, keyboards, laptops, mobile telephones and cordless desk telephones. Each object was treated at least ten times with the disinfectant.

For the execution close to practice a sufficient amount of the disinfectant was put on a clean one-time cloth. The foam applied onto the cloth was applied onto the surface to be disinfected and distributed in such a manner that the surface was completely moistened with a uniform liquid film. In the case of uneven surfaces such as, e.g., keyboards the use as foam is especially suitable since this avoids too much liquid passing into the intermediate spaces. The surface was maintained moist during the entire exposure time.

An optical or functional change of the materials was not determined in any of the objects. Neither did opacity or fissure formations nor separations of (keyboard) letterings or other effects occur that could be traced back to the use of the disinfectant. Even after multiple usage no film formation by constituents of the disinfection solution on the test surfaces could be determined.

The invention claimed is:

1. A method for disinfecting a display screen surface of an electronic device, wherein the display screen surface consists at least partially of temperature-resistant or transparent or highly reflective plastic or plastic coatings, comprising applying to the display screen surface a disinfectant comprising
   25-32 wt % of a mixture of ethanol, 1-propanol and 2-propanol, wherein the amount of each of ethanol, 1-propanol and 2-propanol is at least 5.0 wt % and at the most 15 wt %, and
   0.1-2.0 wt % of an antimicrobial, amphoteric surfactant, and
   water.

2. The method according to claim 1, wherein the disinfectant consists of
   25-32 wt % of a mixture of ethanol, 1-propanol and 2-propanol, wherein the amount of each of ethanol, 1-propanol and 2-propanol is at least 5.0 wt % and at the most 15 wt %, and
   0.1-2.0 wt % of an antimicrobial, amphoteric surfactant and
   66-71.9 wt % water,
whereby the components supplement each other to 100 wt %.

3. The method according to claim 1, wherein th disinfectant contains a mixture of
   13 to 15 wt % ethanol,
   9 to 10.5 wt % 2-propanol,
   5 to 6.5 wt % 1-propanol.

4. The method according to claim 1, wherein the antimicrobial, amphoteric surfactant is N-alkylaminopropyl glycine with alkyl equal to C10 to C16.

5. The method according to claim 1, wherein the electronic device is a flat display screen, laptop display screen, touchscreen, display, mobile telephone display, smart phone, tablet PC or PDA.

6. The method according to claim 1, wherein the plastic or plastic coatings are polycarbonate, polyacrylate and/or polysulfone.

7. The method according to claim 6, wherein on polysulfone surfaces the material compatibility of the disinfectant is measured as ESC potential $\Omega_{ESC}$ according to an alternating ESC test less than 1, for a test time of 25 minutes at 25° C.

8. The method according to claim 7, wherein the material compatibility of the disinfectant is measured as ESC potential $\Omega_{ESC}$ less than 0.8.

9. The method according to claim 6, wherein on polysulfone surfaces the environmental stress cracking $\Delta\Omega_{ESC}$ is below 5, according to the ESC test at a surface temperature of 20° C. to 45° C.

10. The method according to claim 9, wherein on polysulfone surfaces the environmental stress cracking $\Delta\Omega_{ESC}$ is below 4.

11. The method according to claim 9, wherein on polysulfone surfaces the environmental stress cracking $\Delta\Omega_{ESC}$ is below 3.

12. The method according to claim 1, wherein the disinfection effects the eradication of yeasts and/or the eradication of fungi.

13. The method according to claim 12, wherein the yeast is *Candida albicans*.

14. The method according to claim 1, wherein the fungi is *Aspergillus brasiliensis*.

15. The method according to claim 1, wherein the disinfectant brings about a log 4 reduction within 0.5 minutes opposite *Candida albicans* according to the "Standard methods of the DGHM for the testing of chemical disinfection methods" (dated Sep. 1, 2001) in the quantitative suspension test.

16. The method according to claim 1, wherein the disinfectant brings about a log 4 reduction within 15 minutes opposite *Aspergillus brasiliensis* according to the "Standard methods of the DGHM for the testing of chemical disinfection methods" (dated dated Sep. 1, 2001) in the quantitative suspension test.

17. The method according to claim 1, wherein the disinfectant is applied in the form of a foam, a spray disinfectant, a liquid or by a cloth or sponge impregnated with the disinfectant.

18. The method according to claim 1, wherein the disinfectant is applied in the form of a leave-on product.

* * * * *